United States Patent [19]

Seki et al.

[11] Patent Number: 5,397,564
[45] Date of Patent: Mar. 14, 1995

[54] AEROSOL PREPARATION FOR EXTERNAL USE

[75] Inventors: Toshimitsu Seki, Washimiyamachi; Kingo Narumi, Ageo; Tatsuoki Iguchi, Satte; Shozo Kouchiwa, Oomiya, all of Japan

[73] Assignee: Taisho Pharmaceutical Co., Ltd., Japan

[21] Appl. No.: 613,762

[22] PCT Filed: Mar. 16, 1990

[86] PCT No.: PCT/JP90/00350
§ 371 Date: Nov. 13, 1990
§ 102(e) Date: Nov. 13, 1990

[87] PCT Pub. No.: WO90/11068
PCT Pub. Date: Oct. 4, 1990

[30] Foreign Application Priority Data

Mar. 17, 1989 [JP] Japan .................................. 1-63768

[51] Int. Cl.$^6$ ............................................. A61K 9/12
[52] U.S. Cl. .................................... 424/45; 424/47; 424/DIG. 1; 424/78.03
[58] Field of Search ............. 424/45, 47, DIG. 1, 424/78.03

[56] References Cited

U.S. PATENT DOCUMENTS 4,536,323  8/1985  Stopper .............................. 424/45
4,548,807 10/1985  Westfall et al. ..................... 424/45

OTHER PUBLICATIONS

Patent Abstracts of Japan, vol. 6, No. 11 (C-88) [889], 22nd Jan. 1982.
Patent Abstracts of Japan, vol. 13, No. 63 (C-568) [3411], 13th Feb. 1989.

*Primary Examiner*—Thurman K. Page
*Assistant Examiner*—Raj Bawa
*Attorney, Agent, or Firm*—Lorusso & Loud

[57] ABSTRACT

This invention provides an aerosol preparation for topical use, primarily for skin cooling, which is novel in that it is propelled out in the form of a sherbet-like foam. The concentrate is based on water and a lower alcohol and a liquefied. petroleum gases and dimethyl ether is used as a propellant. By using the basic agent and the propellant in a specified ratio, a sherbet-like foam can be formed. The aerosol preparation may also incorporate a drug.

1 Claim, No Drawings

AEROSOL PREPARATION FOR EXTERNAL USE

TECHNICAL FIELD

This invention relates to an aerosol preparation for external use and more specifically, to an aerosol preparation for external cooling which propells a sherbet-like foam.

TECHNICAL BACKGROUND

In recent years, sporting activities have become more and more popular, and with it, injuries such as bruises and wrenches occur frequently, and in many cases, an emergency treatment requires the cooling of the affected part.

Emergency cooling of the affected part is conveniently performed by using an aerosol preparation for external use. Known aerosol agents include, for example, an external aerosol agent composed of a 9:1 mixture of trichloromonofluoromethane and dichlorodifluoromethane (Japanese Patent Publication No. 35797/1970), and an aerosol preparation for external use composed of an organic compound having a molecular weight of at least 80 and a latent heat of evaporation at 25° C. of 20 to 100, filled in a container together with a compressed gas (Japanese Laid-Open Patent No. 86606/1979).

However, aerosol preparations of this type have only a transient cooling effect and its effect does not last long. Moreover since the concentrate and/or propellant uses chlorofluorocarbon, the use of these chemicals are undesirable as the adverse effects of the chlorofluorocarbons have come to be recognized Furthermore, with this type of aerosol preparations the concentrate to be sprayed jets out as a fine mist, its adhesion to the affected part is poor, and the scattered concentrate presents the danger of inhalation by patients.

SUMMARY OF THE INVENTION

It is an object of this invention to provide a foam-forming aerosol preparation having a long-lasting cooling effect with a large amount of the concentrate to be applied without the need for using a fluorocarbon as a propellant.

In order to solve this problem, the present inventors made extensive investigations, and found that when a liquefied petroleum gas, dimethyl ether or a mixture of these gases is adjusted to a specified vapor pressure and used as a propellant and water or a mixture of water with a specified amount of a lower alcohol is used as a concentrate, blending this propellant and the concentrate in a specified ratio an aerosol agent is prepared which when sprayed, sticks to the applied part as a sherbet-like foam, and its cooling effect is high and lasts for a long time.

The aerosol preparation of this invention includes
(A) a propellant having a vapor pressure of 2 to 5 kg/cm$^2$ at 20° C. comprising a liquefied petroleum gas, dimethyl ether or a mixture of these gases, and
(B) a concentrate composed of a mixture of water and the equal weight thereof of a lower alcohol or only water, the weight ratio of (A) to (B) being from 95:5 to 50:50.

In the present invention, liquefied petroleum gas, dimethyl ether or a gaseous mixture of these gases is used as the propellant, and no chlorofluorocarbon, which is likely to destroy the ozone layer, is used.

DESCRIPTION OF THE PREFERRED EMBODIMENTS

The vapor pressure of the propellant should be maintained within the above-specified range, preferably within 2 to 4 kg/cm$^2$.

If the concentrate is composed of water and a lower alcohol, the weight of water may be at least the weight of the lower alcohol. The preferred weight ratio of the alcohol to the water is from 95:5, preferably from 60:40.

The lower alcohols are those having 1 to 4 carbon atoms, preferably ethanol and isopropanol.

As required, there may be used anti-inflammatory agents (e.g., methyl salicylate, monoglycol salicylate, indomethacin, ketoprofen, dichlofenac, ibuprofen and mafenamic acid), antipruritic agents (e.g., ichthammol, mocthammol, thymolic acid, isothipendyl hydrochloride, diphenhydramine hydrochloride and chlorpheniramine), antifungicides (e.g., undecylenic acid, pentachlorophenol, clotrimazole, tolnaftate, trichomycin and miconazole nitrate), germicides (e.g., potassium iodide, chlorhexidine gluconate, acrinol and benzalkonium chloride), antipurulent agents (e.g., penicillin V, tetracycline hydrochloride, fradiomycin and kanamycin), refrigerants (e.g., l-menthol, camphor and mentha oil), anti-oxidants (e.g., BHT), solubilizing agents (diisopropyl adipate, propylene glycol and isopropyl myristate).

In the aerosol preparation of this invention, a nonionic surface-active agent affects the formability of sherbet-like foam and cooling effect of the aerosol. Examples of the non-ionic surface-active agents include polyoxyethylene sorbitan fatty acid esters, sorbitan fatty acid esters, polyoxyethylene polyoxypropylene alkyl ether, polyoxyethylene castor oil, hardened castor oil derivatives, and mixtures of these nonionic surface active agents. The suitable amount of the nonionic surface-active agent is 0.1 to 15% by weight, more preferably 0.5 to 10% by weight.

Since the aerosol preparation of the above composition, when sprayed, forms a sherbet-like foam at the surface of adhesion, the amount of foam adhering increases and its cooling effect is high. There is no inhalation of the mist of the concentrate. Furthermore, since water is formed on the surface of adhesion, it further enhances the cooling effect.

However, if the vapor pressure of the propellant exceeds 5 kg/cm$^2$ the volatilization speed of the propellant increases, and the cooling effect does not rise. If its vapor pressure is less than 2 kg/cm$^2$, the use of the aerosol agent gives an unpleasant feel because of the sagging of the adhering base liquid or the unpleasant sound given off at the time of propelling. If the weight of the lower alcohol in the concentrate increases that of water, it is difficult to form a sherbet-like foam on the surface of adhesion.

If the amount of the concentrate in the aerosol preparation is less than 5% by weight, the same undesirable phenomenon occurs as when the vapor pressure exceeds 5 kg/cm$^2$. When its amount exceeds 50% by weight, the same undesirable phenomenon occurs as does when the vapor pressure of the propellant is less than 2 kg/cm$^2$.

The aerosol preparation of this invention may be prepared by heating and emulsifying the concentrate components to form a concentrate and then filling it together with the propellant into an aerosol container.

The following Examples and Test Examples further illustrate the invention in greater detail.

Example 1

| (Formulation) | |
|---|---|
| l-menthol | 0.5 g |
| Diisopropyl adipate | 0.5 g |
| Polyoxyethylene (60) hardened Castor oil | 0.5 g |
| Purified water-ethanol (95:5) mixture | 8.5 g |
| Liquefied petroleum gas [gauge pressure (20° C.); 2.4 kg/cm$^2$] | 90.0 g |
| | 100.0 g |

The concentrate components were mixed and stirred to dissolve or disperse them uniformly to prepare a concentrate. The concentrate was filled into a pressure-resistant container, and by mounting a valve, the propellant was filled. A propelling spout was attached to form a final product.

Example 2

| (Formulation) | |
|---|---|
| Indomethacin | 0.08 g |
| Diisopropyl adipate | 0.5 g |
| Polyoxyethylene (60) hardened castor oil | 0.5 g |
| Deionized water-ethanol (95:5) mixture | 8.92 g |
| Liquefied petroleum gas [gauge pressure (20° C.); 2.4 kg/cm$^2$] | 90.0 g |
| | 100.0 g |

On the basis of the above formulation, an aerosol agent was prepared in accordance with Example 1.

Example 3

| (Formulation) | |
|---|---|
| isothipendyl hydrochloride | 0.23 g |
| dibucaine hydrochloride | 0.09 g |
| l-menthol | 0.3 g |
| Diisopropyl adipate | 1.5 g |
| Polyoxyethylene (20) sorbitan monooleate | 0.9 g |
| Deionized water-isopropanol (70:30) mixture | 26.98 g |
| Liquefied petroleum gas [gauge pressure (20° C.); 3.2 kg/cm$^2$] | 70.0 g |
| | 100.0 g |

In accordance with the above formulation, an aerosol agent was prepared as in Example 1.

Example 4

| (Formulation) | |
|---|---|
| Mikonasol sulfate | 0.4 g |
| Propylene glycol | 2.0 g |
| Isopropyl myrystate | 2.0 g |
| Polyoxyethylene (20) sorbitan monostearate | 1.2 g |
| Deionized water-ethanol (60:40) mixture | 34.4 g |
| Liquefied petroleum gas-dimethyl ether gas mixture [gauge pressure (30° C.); 2.8 kg/cm$^2$] | 60.0 g |
| | 100.0 g |

In accordance with the above formulation, an aerosol preparation was prepared as in Example 1.

Example 5

| (Formulation) | |
|---|---|
| Indomethacin | 0.3 g |
| Diisopropyl adipate | 4.0 g |
| Polyoxyethylene (20) sorbitan monostearate | 1.2 g |
| Polyoxyethtytlene (20)) sorbitain tristearate | 0.8 g |
| sorbitain monostearate | 1.2 g |
| BHT | 0.1 g |
| l-menthol | 0.1 g |
| Deionized water-ethanol (60:40) mixture | 30 g |
| liquefied petroleum gas-dimethyl ether gaseous mixture [gauge pressure (20° C.); 3.9 kg/cm$^2$] | 62.3 g |
| | 100.0 g |

In accordance with the above formulation, an aerosol preparation was prepared as in Example 1.

Example 6

| (Formulation) | |
|---|---|
| Mikonazol nitrate | 0.4 g |
| l-menthol | 0.27 g |
| Sodium hydroxide | 0.04 g |
| Lactic acid | 0.09 g |
| Sorbitan monostearate Polyoxyethylene (20) | 0.81 g |
| Sorbitan tristearate Polyoxyethylene (20) | 0.81 g |
| Sorbitan monostearate | 0.54 g |
| Deionized water-ethanol (50:50) mixture | 35.0 g |
| Dimethyl ether | 62.04 g |
| | 100.0 g |

In accordance with the aforesaid formulation, an aerosol preparation was prepared as in Example 1.

Test Example 1

(1) An aerosol preparations was prepared as Example 1 except that a 40:60 mixture of deionized water-ethanol was used as the deionized water-ethanol mixture. The resulting aerosol preparation is referred to as a comparative sample A. An aerosol preparation obtained by using a liquefied petroleum gas having a pressure of 5.6 kg/cm$^2$ under a gauge pressure at 20° C. as the propellant in the formulation of Example 1 is referred to as comparative sample B. A comparative sample C was prepared in accordance with the formulation of Example 1 except that the weight ratio of the propellant to the concentrate was changed to 35:65. Ordinary aerosol preparations to be propelled by a mist having the formulations shown as follows were prepared as comparative samples D and E.

| Formulation of a comparative sample D | |
|---|---|
| -menthol | 0.25 g |
| Methyl salicylate | 0.25 g |
| iso-Propyl myristate | 2.0 g |
| Ethanol | 10.5 g |
| Mixed gas of liquefied petroleum gas - dimethyl ether mixture [gauge pressure (20° C.); 3.2 kg/cm$^2$] | 87.0 g |
| | 100.0 g |
| Formulation of a comparative sample E | |

-continued

| | |
|---|---|
| Tocopherol acetate | 0.2 g |
| l-Menthol acetate | 2.0 g |
| Glycol salicylate | 2.0 g |
| Propylene glycol | 2.0 g |
| Ethanol | 58.8 g |
| Mixed gas of liquefied petroleum gas - dimethyl ether mixture [gauge pressure (20° C.); 3.2 kg/cm$^2$] | 35.0 g |
| | 100.0 g |

(2) By using samples 1, 3 and 4 and Comparative samples A, B and C, the formability of sherbet-shaped foam and the coolability of the skin were examined.

The test for foam formability was carried out by spraying each of the samples for 1 second to a petri dish placed 5 cm apart, and the state of formation of a sherbet-shaped foam on the petri dish surface was visually observed, and evaluated in the following three ranks.

○: The formation of much sherbet-shaped foam
Δ: The formation of little sherbet-shaped foam
×: The formation of a sherbet-shaped foam was not observed.

The results are shown in Table 1.

The test for skin cooling effect was performed by a panel of five each of men and women having a normal skin sensation, each sample was allotted to one group, each sample was sprayed for 1 second onto the back of the hand with each sample container placed 5 cm apart from the hand to determine whether the hand sensed coolness or not.

○: Felt very cool.
Δ: Felt cool.
×: Hardly felt cool.

The results are shown by an average value of each of the groups, and are shown in Table 1.

TABLE 1

| | Propellant/ base liquid (weight ratio) | Deionized water/lower alcohol (weight ratio) | Propelling gauge pressure (kg/cm$^2$, 20° C.) | Formability of a sherbet-shaped froth | Skin coolability |
|---|---|---|---|---|---|
| Sample 1 | 90/10 | 95/5 | 2.4 | ○ | ○ |
| Sample 2 | 70/30 | 70/30 | 3.2 | ○ | ○ |
| Sample 3 | 60/40 | 60/40 | 2.8 | ○ | ○ |
| Comparative sample A | 90/10 | 40/60 | 2.4 | × | ○ |
| Comparative sample B | 90/10 | 95/5 | 5.6 | Δ | × |
| Comparative sample C | 35/65 | 95/5 | 2.4 | ○ | × |

Test Example 2

The aerosol preparations prepared in Examples 1 and 5 were designated as samples 1 and 5. In the same way as in Test Example 1, the comparative samples D and E were used. In spray coating on the skin the formability of a sherbet-like foam with a strong effect of cooling and a change in the skin after coating were measured by using thermography. The results are shown in Table 2.

TABLE 2

| | Charges in the temperature of the hand's skin (a decrease in temperature °C. after the lapse of time in minutes) | | | | | | Whether a sherbet-like foam was formed |
|---|---|---|---|---|---|---|---|
| | 0 | ¼ | ½ | 1 | 2 | 3 | |
| Sample 1 | 8.2 | 12.0 | 10.0 | 10.5 | 9.7 | 7.1 | ○ |
| Sample 5 | 7.8 | 11.4 | 9.6 | 9.0 | 8.5 | 5.7 | ○ |
| Comparative sample D | 7.8 | 7.4 | 6.1 | 5.0 | 4.1 | 1.5 | × |
| Comparative sample E | 3.0 | 3.1 | 3.0 | 3.4 | 1.8 | 0.4 | × |

Industrial Utilizability

According to the present invention, there can be provided a sherbet-like foam aerosol preparation having a great skin coolability effect with a large amount of the concentrate adhering without using any chlorofluorocarbon at all as a propellant.

The aerosol preparation of this invention jets out as a sherbet-like foam and the amount of it which scatters as waste is small. Thus, if a drug is incorporated in it, it can be used for the treatment of bruises, wrenches, and athletes' foot as a topical aerosol agent having the pharmacological effect of the drug.

We claim:

1. A sherbet, foam forming aerosol preparation for topical use comprising:
    (A) a propellant selected from the group consisting of liquefied petroleum gas, dimethyl ether and mixtures thereof, said propellant having a vapor pressure of 2 to 5 kg/cm$^2$ at 20° C., and
    (B) water, or a mixture of water and not more than its weight of a lower alcohol having 1–4 carbon atoms and a nonionic surface-active agent,
    the weight ratio of (A):(B) being from 90:10 to 60:40.

* * * * *

UNITED STATES PATENT AND TRADEMARK OFFICE
CERTIFICATE OF CORRECTION

PATENT NO. : 5,397,564
DATED : March 14, 1995
INVENTOR(S) : SEKI et al

It is certified that error appears in the above-indentified patent and that said Letters Patent is hereby corrected as shown below:

<u>In the Abstract:</u>

Line 5, delete the period ".".

Col. 1, line 26, after "100" insert --cal/g--; and
      line 52, before "blending" insert --by--.

Col. 4, line 46, after "as" delete "a".

Signed and Sealed this

Thirty-first Day of October 1995

Attest:

BRUCE LEHMAN

Attesting Officer      Commissioner of Patents and Trademarks